United States Patent
Lok

(10) Patent No.: US 7,851,404 B2
(45) Date of Patent: Dec. 14, 2010

(54) PROCESS FOR PREPARING COBALT CATALYSTS ON TITANIA SUPPORT

(75) Inventor: Cornelis Martinus Lok, Cleveland (GB)

(73) Assignee: Johnson Matthey PLC, London (GB)

( * ) Notice: Subject to any disclaimer, the term of this patent is extended or adjusted under 35 U.S.C. 154(b) by 1435 days.

(21) Appl. No.: 10/528,527

(22) PCT Filed: Sep. 25, 2003

(86) PCT No.: PCT/GB03/04109

§ 371 (c)(1), (2), (4) Date: Mar. 18, 2005

(87) PCT Pub. No.: WO2004/028687

PCT Pub. Date: Apr. 8, 2004

(65) Prior Publication Data

US 2005/0272827 A1 Dec. 8, 2005

(30) Foreign Application Priority Data

Sep. 25, 2002 (GB) ................................ 0222240.4

(51) Int. Cl.
*B01J 23/00* (2006.01)
(52) U.S. Cl. ..................... 502/326; 502/350
(58) Field of Classification Search .............. 502/326, 502/350; 518/716; 568/950, 959
See application file for complete search history.

(56) References Cited

U.S. PATENT DOCUMENTS

| 4,255,357 A | 3/1981 | Gardner et al. |
|---|---|---|
| 4,595,703 A | 6/1986 | Payne et al. |
| 4,605,679 A | 8/1986 | Kobylinski et al. |
| 4,717,702 A | 1/1988 | Beuther et al. |
| 5,545,674 A | 8/1996 | Behrmann et al. |
| 5,874,381 A | 2/1999 | Bonne et al. |
| 5,968,991 A | 10/1999 | Mauldin |
| 6,130,184 A | 10/2000 | Geerlings et al. |
| 6,534,436 B2 | 3/2003 | Lok et al. |
| 6,927,190 B2 * | 8/2005 | Lok et al. .................. 502/327 |
| 7,368,625 B2 * | 5/2008 | Lok et al. .................. 585/733 |
| 7,452,844 B2 * | 11/2008 | Hu et al. .................... 502/327 |
| 2003/0119668 A1 | 6/2003 | Lok et al. |

FOREIGN PATENT DOCUMENTS

| EP | 0 013 275 B1 | 7/1980 |
|---|---|---|
| EP | 0 092 878 A2 | 11/1983 |
| EP | 0 266 898 A3 | 5/1988 |
| EP | 1 163 955 A1 | 12/2001 |
| EP | 0 775 081 B1 | 6/2002 |
| GB | 926235 | 5/1963 |
| JP | 05-168932 | 7/1993 |
| WO | WO-96/04072 | 2/1996 |
| WO | WO-98/47617 | 10/1998 |
| WO | WO-01/62381 A1 | 8/2001 |
| WO | WO-02/089978 A1 | 11/2002 |
| WO | WO-03/024905 A1 | 3/2003 |

OTHER PUBLICATIONS

Oukaci et al., "Comparison of patented CO F-T catalysts using fixed-bed and slurry bubble column reactors," *Applied Catalysts A: General*, 186 (1999), pp. 129-144.
Liu Fu et al., "Structure Sensitivity and Its Effects on Product Distribution in CO Hydrogenation on Cobalt/Alumina," *Journal of Catalysis*, vol. 92, 1985, pp. 376-387.
Byron G. Johnson et al., "The Role of Surface Structure and Dispersion in CO Hydrogenation on Cobalt," *Journal of Catalysis*, vol. 128, 1991, pp. 231-247.
International Search Report dated Aug. 3, 2001, from International Application No. PCT/FB01/01811.
Internation Search Report dated Jun. 25, 2001, from International Application No. PCT/GB01/00702.

* cited by examiner

*Primary Examiner*—Cam N Nguyen
(74) *Attorney, Agent, or Firm*—RatnerPrestia

(57) ABSTRACT

Catalysts comprising cobalt on a titania support are produced by mixing together particles of a solid titania support and an aqueous solution of cobalt ammine carbonate, and heating to an elevated temperature sufficient to effect decomposition of the cobalt ammine carbonate and precipitation of a cobalt species onto said support. The catalysts are useful in hydrogenation and Fischer-Tropsch reactions.

14 Claims, No Drawings

PROCESS FOR PREPARING COBALT CATALYSTS ON TITANIA SUPPORT

This application is the U.S. national phase application of PCT International Application No. PCT/GB2003/004109, filed Sep. 25, 2003, and claims priority of British Patent Application No. 0222240.4, filed Sep. 25, 2002.

FIELD OF THE INVENTION

This invention relates to cobalt catalysts comprising cobalt supported on a solid titania support and in particular to a method for manufacturing such catalysts.

BACKGROUND OF THE INVENTION

Catalysts comprising cobalt on a support such as silica or alumina are known in the art for hydrogenation reactions, e.g. for the hydrogenation of chemicals such as aldehydes and nitriles and for the preparation of hydrocarbons from synthesis gas via the Fischer-Tropsch reaction.

WO-A-96/04072 discloses a cobalt on transition alumina catalyst containing between 3 and 40% by weight of cobalt and having a cobalt surface area greater than 30 $m^2$/g cobalt.

EP-A-0013275 discloses coprecipitated cobalt-silica hydrogenation catalysts prepared by adding an alkaline precipitating agent to a heated mixture containing cobalt cations, silicate anions and solid porous carrier particles under agitation thereby to precipitate the cobalt and silicate ions onto the solid support particles.

WO-A02/089978 describes a catalyst for use in the Fischer-Tropsch process, comprising at least one metal selected from the group consisting of nickel, cobalt, iron, ruthenium, osmium, platinum, palladium, iridium, rhenium, molybdenum, chromium, tungsten, vanadium, rhodium, copper, zinc, and combinations thereof and at least one promoter, said metal and promoter being dispersed on a support to form a catalyst particle. The preferred support is alumina. The particles have a BET surface area of from about 100 $m^2$/g to about 250 $m^2$/g, and the metal and promoter are dispersed on the support such that the crystallite size of the metal oxide is from about 40 Å to about 200 Å.

In certain reactions it may be beneficial to use cobalt deposited on a titania support rather than cobalt on alumina. For example, as reported by Oukaci et al (Applied Catalysis A: General 186 (1999) 129-144)), cobalt supported on titania is preferred by some workers for Fischer-Tropsch reactions because it is more active for CO hydrogenation than cobalt catalysts supported on alumina or silica or other supports. Furthermore titania supported catalyst may be preferred for use in acid reaction media where gamma alumina supports may show a tendency to dissolve to some extent.

U.S. Pat. No. 5,968,991 describes a process for the preparation of a catalyst useful for conducting carbon monoxide hydrogenation reactions, especially a Fischer-Tropsch catalyst In the preparation of the catalyst, a solution of a multifunctional carboxylic acid having from about 3 to 6 total carbon atoms, especially glutamic or citric acid, is employed to impregnate and disperse a compound or salt of rhenium and a compound or salt of a catalytic metal, or metals, e.g., copper or an Iron Group metal such as iron, cobalt, or nickel onto a refractory inorganic oxide support such as titania. This method of preparation requires-repeated impregnations in order to achieve the desired cobalt loadings.

U.S. Pat. No. 6,130,184 describes a process for the preparation of a cobalt-containing catalyst or catalyst precursor, comprising mixing titania or a titania precursor, a liquid, and a cobalt compound, which is at least partially insoluble in the amount of liquid used, to form a mixture, shaping and drying of the mixture thus-obtained, followed by calcination.

U.S. Pat. No. 5,545,674 describes a process for preparing cobalt catalysts supported on titania spheres by spraying the hot titania spheres with an aqueous cobalt nitrate and perrhenic acid mixture, optionally after soaking the support spheres in a non-aqueous liquid to provide a non-uniformly distributed cobalt catalyst.

U.S. Pat. No. 4,595,703 describes a cobalt-titania catalyst, or thoria promoted cobalt-titania catalyst used in a Fischer-Tropsch process wherein cobalt, or cobalt and thoria, is composited, or dispersed upon titania, $TiO_2$, or a titania-containing carrier, or support, wherein the support contains a rutile: anatase ratio of at least about 2:3, and preferably at least about 3:2.

In comparison with other catalytic metals such as copper and nickel used for hydrogenation reactions, cobalt is a relatively expensive and so, to obtain the optimum activity, it is desirable that as much as possible of the cobalt present is in an active form accessible to the reactants. It is therefore desirable to maximise the surface area of the cobalt in the supported catalysts. It is desirable to manufacture a cobalt catalyst supported upon titania which is useful in the Fischer-Tropsch process by depositing a relatively high loading of well-dispersed cobalt species upon the support.

SUMMARY OF THE INVENTION

Accordingly we now provide a process for manufacturing a catalyst which comprises a cobalt species on a solid titania support, comprising mixing together particles of a solid titania support and an aqueous solution of cobalt ammine carbonate, and heating to an elevated temperature sufficient to effect decomposition of the cobalt ammine carbonate and precipitation of cobalt compounds onto said support.

In one embodiment of the invention we provide a method of making a catalyst comprising a cobalt species on a titania support, comprising the steps of mixing a titania particulate material with an aqueous solution of a soluble cobalt compound, heating the mixture of particulate material and cobalt compound to effect precipitation of cobalt compounds on the titania, filtering the solid residue from the aqueous medium, and drying.

In a further embodiment of the invention we also provide a process for the production of a catalyst comprising saturating a titania catalyst support with an aqueous solution of cobalt ammine carbonate, and removing the excess of the solution, before heating the resulting product to a temperature sufficient to effect decomposition of the cobalt ammine carbonate.

The solid residue comprising the catalyst may optionally be calcined and, optionally, reduced.

DETAILED DESCRIPTION OF THE INVENTION

The term "cobalt species" is used broadly to include both elemental cobalt and cobalt in combined form, e.g. as compounds such as cobalt oxides and cobalt hydroxycarbonates. The cobalt compounds which are precipitated on the support as a result of heating the aqueous solution of soluble cobalt compound comprise basic cobalt carbonate species and/or cobalt oxides.

The catalyst is normally used in its reduced form, i.e. in which a major proportion of the cobalt species is reduced to metallic cobalt. The catalyst may, however, be provided as a precursor wherein the cobalt is present as one or more compounds, such as oxides or hydroxy carbonates, reducible to elemental cobalt. In this form, the material may be a catalyst precursor and may be treated to reduce the cobalt compounds to metallic cobalt. Alternatively the oxidic material may itself be useful as a catalyst and used as supplied, e.g. for oxidation reactions. The cobalt surface area figures used herein apply to the material after reduction, but the invention is not limited to the provision of reduced catalyst.

By the term total cobalt, we mean the amount of cobalt whether present in elemental or combined form. Generally however at least 70% by weight of the total cobalt in the reduced catalyst will be in the elemental state.

The catalysts of the invention preferably have a cobalt to titanium atomic ratios in the range 0.01 to 50, particularly 0.03 to 25 and especially 0.05 to 10.

The titania may be formed from natural sources or may be a synthetic, e.g. precipitated titania. The titania may be in the form of a powder or a shaped granular material, e.g. as extruded or tabletted titania pieces. In shaped forms, the support may additionally comprise forming aids such as a lubricant and/or binder. The titania may optionally comprise up to 20% by weight of another refractory oxide material, typically silica, alumina or zirconia. The titania may alternatively be present as a coating on a support which is preferably of silica or alumina, typically as a coating of 0.5 to 5 monolayers of titania upon the underlying support. Therefore when we refer to titania we include titania-coated supports.

Suitable powdered titanias typically have particles of surface weighted mean diameter D[3,2] in the range 1 to 100 μm, particularly 3 to 100 μm. If desired, the particle size may be increased by slurrying the titania in water and spray drying. Preferably the BET surface area of the particles is in the range 10 to 500 $m^2/g$. Conventional titania supports for F-T catalysts are based upon rutile forms of titania, which has superior attrition resistance compared with anatase forms. These titanias are normally of relatively low surface area, e.g. about 10-100 $m^2/g$. Higher surface area titania catalyst supports, having surface areas >300 $m^2/g$ are now available commercially and these are very suitable for use in the present invention.

Granular titanias may have a variety of shapes and particle sizes, depending upon the mould or die used in their manufacture. For example the particles may have a cross-sectional shape which is circular, lobed or other shape and a length from about 1 to 10 mm. The surface area is generally in the range 10-500 $m^2/g$, preferably 100 to 400 $m^2/g$.

The pore volume of the titania is generally between about 0.1 and 4 ml/g, preferably 0.2 to 2 ml/g and the mean pore diameter is preferably in the range from 2 to about 30 nm.

The cobalt compound is most preferably a cobalt ammine complex which is formed in situ in aqueous solution by dissolving basic cobalt carbonate in a solution of ammonium carbonate in aqueous ammonium hydroxide, to give a product of the desired cobalt content. The cobalt ammine carbonate solution may be made by dissolving basic cobalt carbonate in an aqueous solution of ammonium carbonate or ammonium carbamate containing additional ammonium hydroxide. The relative amounts should be such that the pH of the solution is in the range 7.5 to 12, preferably 9 to 12. The solution preferably contains 0.1 to 2.5 moles of the cobalt complex per litre. As the concentration of cobalt increases, then generally the proportion of carbonate ions relative to hydroxide ions in the basic cobalt carbonate feed should be increased. Additional ammonium hydroxide solution may be added in order to provide a slurry of handleable viscosity when the support particles are mixed in. The cobalt ammine complex compound is then heated, e.g. to a temperature in the range 60 to 110° C., to cause the cobalt ammine complex to decompose with the evolution of ammonia and carbon dioxide and to deposit a cobalt compound on the surface, and in the pores, of the titania. This step is conveniently carried out when slurrying titania powders with the cobalt compound so that the slurry is then maintained at the elevated temperature for a period, hereinafter the ageing period. The solid material is then filtered from the aqueous medium, washed and dried. Using this form of the process of the invention, a catalyst having a high cobalt dispersion and a high cobalt loading, e.g. >10% cobalt, (more preferably >15% cobalt, by weight) may be prepared in a single deposition step.

The amount of cobalt in the catalyst may be varied by varying the relative amount of cobalt and support present in the reaction mixture and by controlling the concentration of the solution of cobalt compound.

Alternatively the cobalt compound is absorbed into the pore structure of the titania particle by impregnating titania particles with the solution of cobalt compound. The particles may then conveniently be separated from the remaining solution and the ageing process may be carried out by heating them e.g. to a temperature above 100° C. for the ageing period of at least 60 minutes, preferably at least 100 minutes to decompose the cobalt compound held within the particles to deposit cobalt species in the structure of the titania particle. The particle may be subjected to successive impregnations, e.g. by separating them from the impregnation solution and drying before a subsequent impregnation.

The solid material may then be calcined in air, e.g. at a temperature in the range 250 to 450° C., to decompose the cobalt compound to cobalt oxide. The resultant catalyst precursor may be then reduced, e.g. with hydrogen, at a temperature between 300 to 550° C., more preferably below about 500° C., e.g. 330-420° C. Upon reduction, most, if not all, of the cobalt oxide is reduced to metallic cobalt; the result is cobalt metal in a highly dispersed form, i.e. having a high cobalt surface area. Alternatively the cobalt compound may be directly reduced, i.e. without the need for a calcination step.

Preferably the amounts of titania and cobalt ammine carbonate employed are such that the cobalt to titanium atomic ratio is in the range 0.03 to 5. Irrespective of the cobalt content of the catalyst, the particle size of the catalyst is essentially the same as the particle size of the titania.

The catalysts of the invention preferably contain 3 to 75% by weight of total cobalt. When a low surface area form of titania is used, i.e. having a BET area of <100 $m^2/g$, then the cobalt content may more usually be below 40% by weight total cobalt, e.g. 5-35% by weight total cobalt. The amount of cobalt which is desirable varies according to the type of reaction for which the catalyst is used. Selection of an appropriate amount of cobalt is easily determined or known by the skilled person. Preferred catalysts typically have a cobalt surface area in the range 15 to 100, particularly 20 to 40 $m^2$ per gram total cobalt.

The cobalt surface area is determined by $H_2$ chemisorption. The sample (about 0.5 g) is degassed and dried under vacuum at 120° C. and then reduced by heating to 425° C. (unless specifically mentioned otherwise) at a rate of 3° C. per minute whilst hydrogen gas is passed through the sample at a flow rate of 250 ml/min for 18 hours. The sample is then heated under vacuum to 450° C. over 10 minutes and maintained under those conditions for 2 hours. Following this pretreatment, the chemisorption analysis is carried out at 150° C. using pure $H_2$ gas. The full isotherm is measured up to 800 mm Hg pressure of $H_2$ and the straight line portion of the chemisorption isotherm between 300 and 800 mm Hg is extrapolated to zero pressure to calculate the volume of the gas (V) which is chemisorbed by the sample. The metal surface area is then calculated from the following equation:

Cobalt surface area=$(6.023\times10^{23}\times V\times SF\times A)/22414$ where V=uptake of $H_2$ in ml/g
SF=Stoichiometry factor (assumed 2 for $H_2$ chemisorption on Co)
A=area occupied by one atom of cobalt (assumed 0.0662 $nm^2$)

This method of calculating cobalt surface area is described in the Operators Manual for the Micromeritics ASAP 2000 Chemi System V 1.00, Appendix C, (Part no 20042808-01, 18th January 1991)

For hydrogenation reactions, the active form of the cobalt is elemental cobalt although in the active catalyst only some, rather than all, of the cobalt is normally reduced to the elemental form. Hence a useful measure is the exposed surface area of elemental cobalt per g of total cobalt present. Except where expressly indicated, as used herein, total cobalt contents are expressed as parts by weight of cobalt (calculated as cobalt metal, whether the cobalt is actually present as the metal or is in a combined form, e.g. as cobalt oxides) per 100 parts by weight of the catalyst or precursor thereto.

Useful catalyst products are formed by the dried precipitated product, a calcined (oxidic) product or a reduced product, depending on the use for which the catalyst is made.

When a catalyst composition requires a step such as calcination and/or reduction to produce the active form of catalyst for the desired reaction, it may be referred to as a catalyst precursor.

In a non-reduced form the catalysts may be useful in oxidation reactions e.g. to oxidise organic compounds, for example as in the treatment of effluent containing organic material.

The catalyst compositions of the invention may optionally include one or more promoter metals. Suitable promoter metals include boron, cerium, chromium, copper, iridium, iron, lanthanum, manganese, molybdenum, palladium, platinum, rhenium, rhodium, ruthenium, strontium, tungsten, vanadium, zinc, sodium, potassium, rubidium, caesium, magnesium, titanium, zirconium, and other rare earth metals and combinations thereof. The selection of a promoter metal is dependent upon the desired use of the catalyst. A preferred promoter is rhenium which appears to promote the formation of high cobalt surface areas in the reduced catalyst.

The catalysts, in reduced form, may be used for hydrogenation reactions such as the hydrogenation of aromatic or olefinic compounds, e.g. waxes, nitro, nitrile or carbonyl compounds, e.g. the conversion of nitrobenzene to aniline or the conversion of fatty nitriles to amines or the hydrogenation of aldehydes to the corresponding alcohols. They may also be used for the hydrogenation of paraffin waxes to remove traces of unsaturation therein. They may also be useful in a wide range of other reactions, for example the Fischer-Tropsch process, i.e. where hydrogen and carbon monoxide are reacted in the presence of the catalyst to form higher hydrocarbons. This may be part of an overall process for the conversion of natural gas to petroleum compounds wherein the hydrogen/carbon monoxide gas mixture is a synthesis gas formed by steam reforming natural gas.

The catalyst may be provided in the form of a concentrate of the catalyst particles dispersed in a suitable carrier medium, e.g. hardened soybean oil or a hydrocarbon wax. Preferably the amount of catalyst in said concentrate is such that the concentrate has a total cobalt content of 3 to 30%, preferably 5 to 15% by weight. The catalyst may alternatively be subjected to a process to form shaped pieces such as by granulation, tabletting, extrusion or other known methods, optionally with the addition of processing aids such as lubricants or binders.

When the catalyst is to be used in a reduced form, it may be supplied in non-reduced form, i.e. as a catalyst precursor, to be reduced in-situ before use or alternatively the catalyst may be reduced and then passivated in order to protect the reduced metal during subsequent storage and transport. Methods of protecting the catalyst are well known.

The invention is illustrated by the following examples in which the stock solution employed was made up using 1707 g ammonia solution (SG 0.89, 30% ammonia), 198 g ammonium carbonate, 218 g basic cobalt carbonate (46.5% wt % Co, bulk density 0.640 g/ml) and 1877 g demineralised water. The total volume of the stock solution was 4 litres.

The carrier employed was P25 titania supplied by Degussa, having a surface area of 50.6 $m^2/g$ (as measured by BET methodology) and a pore volume (as determined by nitrogen porosimetry from the P/Po=0.980 values of the desorption isotherm) of about 0.14 mug and having a mean diameter D[3,2] of 1.7 μm. The average pore diameter, calculated as 4*Vp/SBET, where Vp is the pore volume ($m^3/g$) and SBET is the BET surface area ($m^2/g$), was about 11 nm. The phase ratio of this titania is about 83% anatase and 17% rutile.

EXAMPLE 1

A portion of the stock solution was diluted with 7 parts by volume of a 9 wt % ammonia solution per part by volume of the stock solution in order to reduce the viscosity of the slurry produced by mixing the solution with the carrier particles. The pH of the diluted stock solution was 11.1.

The titania carrier particles and an amount of the diluted stock solution corresponding to a nominal 5% by weight of cobalt, based on the weight of the Utania particles, were charged to a stirred vessel equipped with a condenser for removal of liquid by distillation. The mixture was heated to boiling while stirring and gentle boiling at about 96° C. was maintained for a period of time. After about 90 min total heating time the solution became clear. After a total heating time of 130 min part of the mixture was filtered and the solid recovered, washed and then dried in air at 110° C. overnight so give sample A.

The gentle boiling was continued for the remaining portion of the mixture for a further 20 min (to give a total heating time of 150 min) and then the mixture was filtered and the solid recovered, washed and then dried in air at 110° C. overnight so give sample B.

The resultant catalyst precursors A and B were then reduced by passing hydrogen through a bed of the catalyst while heating to 425° C. The cobalt surface area was determined by $H_2$ chemisorption as described hereinbefore.

EXAMPLE 2

Example 1 was repeated, but using undiluted stock solution and total heating times of 130 and 150 min. The amount of stock solution employed was such as to give a nominal 10% by weight of cobalt, based on the weight of the titania particles.

EXAMPLE 3

Example 1 was repeated but using 1 part by volume of the 9 wt % ammonia solution per part by volume of the stock solution, and an amount of the diluted stock solution such as to give a nominal 15% by weight of cobalt, based on the weight of the titania particles. The total heating times were 120, 140 and 160 min.

EXAMPLE 4

Example 2 was repeated, using undiluted stock solution in such an amount that the nominal cobalt content was 20% by weight based on the weight of the titania particles. The total heating times were 70, 95, 120 and 135 min.

EXAMPLE 5

Example 1 was repeated but using 1 part by volume of the 9 wt % ammonia solution per part by volume of the stock solution, and an amount of the diluted stock solution such as to give a nominal 25% by weight of cobalt, based on the weight of the titania particles. The total heating times were 60, 80 and 100 min.

The cobalt content of the reduced catalyst was calculated from the measured cobalt content of the unreduced material and the weight difference between the unreduced material and the reduced catalyst. The chemisorption results are shown in Table 1.

A sample of the precursor, i.e. before reduction, of Example 4D was subjected to temperature programmed reduction in a 5% hydrogen in nitrogen gas stream. The sample was first heated to 120° C. to remove moisture and thereafter from 120 to 1000° C. in the hydrogen stream at a heating rate of 5° C. per minute. The change in concentration of hydrogen between the inlet gas and the outlet gas was monitored by a katharometer to show the consumption of hydrogen at each temperature. The results showed peaks at 195° C., 275° C. and 435° C. The 275° C. peak probably is reduction of $Co_3O_4$ to CoO while the 435° C. peak corresponds to reduction of CoO to the cobalt metal. There is no evidence for any species reducing at high temperatures suggesting that all cobalt may be reducible and that there is little unreducible cobalt titanate formation.

As a comparison, a catalyst comprising 20% Co on a gamma alumina support (Puralox™ HP14/150, available from Sasol), prepared by a similar method was subjected to temperature programmed reduction under the same conditions. The corresponding peaks occur at about 225, 295 and 600° C. respectively. Additionally a small, broad peak is present at 800-900° C., indicating the presence of a difficulty reducible cobalt compound, which is believed to be cobalt aluminate. Thus the cobalt catalysts on a titania support are more readily reducible than the comparable catalyst on an alumina support.

EXAMPLES 6-10

Catalysts were made by the method described in Example 1, using the P25 titania support which had been calcined at 730° C. for 4 hours to increase the rutile phase content. The calcined support consisted of about 75% rutile and 25% anatase forms of titania. The stock solution was diluted, where necessary, with a 30% aqueous ammonia solution in order to ensure that the slurry was of a convenient viscosity, and the amount of titania and solution was adjusted to provide the required final cobalt content. The results are shown in Table 2.

TABLE 1

| | | Cobalt content (% wt) | | Cobalt surface area | |
|---|---|---|---|---|---|
| Example | Heating time (min) | Precursor before reduction | Reduced catalyst | $m^2$ per g of reduced catalyst | $m^2$ per g of cobalt |
| 1A | 130 | 5.5 | 5.8 | 1.0 | 17 |
| 1B | 150 | 5.4 | 5.6 | 1.4 | 25 |
| 2A | 130 | 10.1 | 11.0 | 2.5 | 23 |
| 2B | 150 | 10.0 | 11.0 | 1.9 | 17 |
| 3A | 120 | 15.9 | 17.8 | 4.1 | 23 |
| 3B | 140 | 16.0 | 17.8 | 3.9 | 22 |
| 3C | 160 | 16.0 | 17.8 | 3.8 | 21 |
| 4A | 70 | 16.1 | 18.1 | 4.6 | 25 |
| 4B | 95 | 20.8 | 24.2 | 4.0 | 17 |
| 4C | 120 | 21.1 | 24.6 | 5.4 | 22 |
| 4D | 135 | 21.1 | 24.6 | 5.1 | 21 |
| 5A | 60 | 26.4 | 31.4 | 6.4 | 20 |
| 5B | 80 | 27.4 | 32.7 | 4.1 | 13 |
| 5C | 100 | 27.7 | 32.5 | 5.7 | 18 |

TABLE 2

| Cobalt content (% wt) | Cobalt surface area |
|---|---|

| Example | Heating time (min) | Precursor before reduction | Reduced catalyst | $m^2$ per g of reduced catalyst | $m^2$ per g of cobalt |
|---|---|---|---|---|---|
| 6A | 75 | 7.0 | 7.2 | 1.7 | 23.8 |
| 6B | 90 | 7.1 | 7.4 | 2.0 | 27.0 |
| 6C | 105 | 7.2 | 7.5 | 2.3 | 30.5 |
| 6D | 120 | 7.1 | 7.5 | 2.0 | 26.7 |
| 6E | 150 | 7.3 | 7.8 | 1.9 | 24.4 |
| 7A | 75 | 10.1 | 10.8 | 2.3 | 21.2 |
| 7B | 90 | 9.9 | 10.6 | 2.5 | 23.5 |
| 7C | 105 | 9.8 | 10.2 | 2.3 | 22.5 |
| 7D | 120 | 9.9 | 10.7 | 2.3 | 21.5 |
| 7E | 150 | 9.6 | 10.2 | 1.9 | 18.7 |
| 8A | 85 | 13.2 | 14.4 | 2.7 | 18.8 |
| 8B | 100 | 13.8 | 15.1 | 2.9 | 19.2 |
| 8C | 115 | 13.7 | 15.0 | 3.4 | 22.7 |
| 8D | 130 | 13.6 | 15.0 | 2.6 | 17.4 |
| 8E | 150 | 13.9 | 14.9 | 3.4 | 22.8 |
| 9A | 90 | 21.6 | 25.1 | 3.6 | 14.3 |
| 9B | 105 | 21.8 | 25.3 | 3.3 | 13.0 |
| 9C | 120 | 21.9 | 25.7 | 3.8 | 14.8 |
| 9D | 135 | 22.1 | 25.6 | 3.3 | 12.9 |
| 9E | 150 | 21.4 | 24.6 | 4 | 16.3 |
| 10A | 75 | 22.6 | 26.6 | 3.9 | 14.7 |
| 10B | 90 | 22.4 | 26.0 | 3.2 | 12.3 |
| 10C | 105 | 22.8 | 26.4 | 3.6 | 13.6 |
| 10D | 120 | 22.3 | 25.9 | 3.5 | 13.5 |
| 10E | 150 | 22.7 | 25.7 | 4.5 | 17.5 |

EXAMPLE 11

A cobalt on titania catalyst containing 20% cobalt by weight, made according to Example 1, was impregnated with a 45% aqueous perrhenic acid solution by spraying the solution into a rotating drum containing the catalyst. The quantity of solution was calculated to give 1% rhenium by weight of catalyst. The surface area was measured using hydrogen chemisorption as described earlier and the results for the Re-promoted and un-promoted catalyst are shown in Table 3. The surface area was measured for a reduction temperature of 425° C. and also for a sample reduced at 350° C. Temperature programmed reduction of the Re-containing catalyst showed the major cobalt oxide reduction peak maximum at about 400° C. compared with about 435° C. for the catalyst containing no rhenium.

TABLE 3

| Example 11 | % wt Re (before reduction) | Cobalt content (% wt) | | | Cobalt surface area | | | |
|---|---|---|---|---|---|---|---|---|
| | | Precursor before reduction | Reduced catalyst (425° C.) | Reduced catalyst (350° C.) | 425° C. | | 350° C. | |
| | | | | | $(m^2g^{-1}$ cat) | $(m^2g^{-1}$ Co) | $(m^2g^{-1}$ cat) | $(m^2g^{-1}$ Co) |
| unpromoted | — | 19.5 | 22.9 | 21.7 | 4.8 | 20.9 | 7.2 | 33.2 |
| Re doped | 1.0 | 19.5 | 22.4 | 21.6 | 5.4 | 24.1 | 6.2 | 28.7 |

EXAMPLE 12

The performance of the catalyst of Example 5C was tested in a Fischer Tropsch reaction.

The catalyst (10 g) was first reduced in a fixed reactor at 400° C. for 4 h using 700 ml/min H2. 7.6 g reduced catalyst was then transferred to a 1 litre CSTR and re-reduced in-situ at 230° C. for 15 hours using 5 Standard l/h/g cat of hydrogen before starting the Fischer-Tropsch reaction at 20 bar and 180° C. while raising the temperature to 210° C. in 3 hours. The flow of the gas mixture (molar ratio $H_2$: CO 2.1:1) was then adjusted to reach approximately 50% conversion. At a space velocity of 5 Standard l/h/g cat $H_2$ and after 48.5 h, the following performance was observed—51.4% conversion of CO, with the following selectivities to different products; 4.3% to $CH_4$, 0.3% to $CO_2$, 1.67% to $C_2$-$C_4$ olefins, 1.42% to $C_2$-$C_4$ paraffins and 92.31% to $C_5$+ organic compounds. As a comparison cobalt on alumina catalysts made by a similar process were tested under the same conditions and the selectivities are shown in Table 4.

EXAMPLE 13

Catalysts were made using the method of the invention in which the support was a titania-coated alumina. The support was prepared by diluting 128 g tetraisopropyl titanate (VERTEC™ TIPT) in 1000 g isopropanol and then mixing with 400 g of a gamma alumina (Puralox™ HP14/150, available from Sasol) at 45° C. for 30 minutes in a rotary evaporator. The isopropanol is then removed by distillation and the temperature is increased to 90° C. and the pressure reduced to a vacuum. The resulting particles were calcined at 400° C. for 8 hours after drying at 120° C. for at least 15 hours. The support contained 5.4% Ti based on the weight of alumina. Samples 13 A and 13B were made using these supports using the method described in Example 1.

TABLE 4

|  | Example 5C | Comp A | Comp B |
|---|---|---|---|
| Co % (reduced catalyst) | 27.7 | 32.8 | 19.3 + 1% Re |
| Support | titania | theta alumina | gamma alumina |
| CO conversion (%) | 54 | 61 | 49 |
| Sel (CH$_4$) % | 4.3 | 6.5 | 8.2 |
| Sel (CO$_2$) % | 0.3 | 0.2 | 0.4 |
| Sel (C$_2$-C$_4$ olefin) % | 1.7 | 4.5 | 3.9 |
| Sel (C$_2$-C$_4$ paraffin) % | 1.4 | 6.0 | 6.5 |
| Sel (C$_{5+}$ organics) % | 92.3 | 81.8 | 82.0 |

EXAMPLE 14

400 g of Puralox™ HP14/150 alumina was mixed with a solution of 138 g of 76% aqueous titanium lactate diluted in 2500 g of deionised water for 30 minutes. The resulting slurry was adjusted to pH 9.5 using 192 g of 14% ammonia solution. The solids were then removed by vacuum filtration, re-slurried in water and washed twice in 2 litres of deionised water. The resulting particles were calcined at 400° C. for 8 hours after drying at 120° C. for at least 15 hours. The support contained 5.4% Ti based-on the weight of alumina. The support was then used to prepare catalysts 14 A and 14B by the method described in Example 1. The cobalt surface areas were determined by H$_2$ chemisorption as described above and the results are shown in Table 5.

TABLE 5

| Example | Heating time (min) | Cobalt content (% wt) | | Cobalt surface area | |
|---|---|---|---|---|---|
|  |  | Precursor before reduction | Reduced catalyst | m$^2$ per g of reduced catalyst | m$^2$ per g of cobalt |
| 13A | 110 | 14.6 | 16.5 | 12.3 | 74.4 |
| 13B | 110 | 29.6 | 38.0 | 21.1 | 55.5 |
| 14A | 110 | 15.5 | 17.6 | 12.2 | 69.3 |
| 14B | 110 | 30.7 | 41.0 | 21.8 | 53.5 |

The invention claimed is:

1. A process for manufacturing a catalyst which comprises a cobalt species on a titania support having upon reduction at 425° C., a cobalt metal surface area, as measured by hydrogen chemisorption at 150° C., in the range from 15 to 100 m$^2$ per gram total cobalt, comprising mixing together said titania support and an aqueous solution of cobalt ammine carbonate at a pH in the range 7.5 to 12, and then heating to a temperature in the range 60 to 110° C. to effect decomposition of the cobalt ammine carbonate and precipitation of an insoluble cobalt compound onto said titania support, wherein the pH is maintained above 7.5 during the heating step, further comprising directly reducing the cobalt compound without a calcining step.

2. A process according to claim 1, comprising saturating a titania support with an aqueous solution of cobalt ammine carbonate, and removing the excess of the solution, before heating the resulting product to a temperature sufficient to effect decomposition of the cobalt ammine carbonate.

3. A process according to claim 1, wherein the mixture of titania support and said cobalt solution is heated to a temperature sufficient to effect decomposition of the cobalt ammine carbonate in situ before separating the solid catalyst from the mixture and drying.

4. A process according to claim 3 further comprising filtering a solid material from the aqueous solution, drying the solid material, and directly reducing the cobalt compound without a calcining step.

5. A process according to claim 1, wherein the titania support and cobalt solution are maintained at an elevated temperature for a period of at least 60 minutes.

6. A process according to claim 1 wherein the step of reducing the resulting catalyst product is performed with hydrogen at a temperature between 300 to 550° C.

7. A process according to in claim 6, further comprising the step of dispersing the reduced catalyst product in particulate form in a carrier matrix.

8. A process according to claim 1 wherein the titania support and aqueous solution of cobalt ammine carbonate are mixed at a pH in the range 9 to 12.

9. A process for manufacturing a catalyst which comprises elemental cobalt on a titania support having, upon reduction at 425° C., a cobalt metal surface area, as measured by hydrogen chemisorption at 150° C., in the range from 15 to 100 m$^2$ per gram total cobalt, comprising mixing together said titania support and an aqueous solution of cobalt ammine carbonate at a pH in the range 9 to 12, then heating to a temperature in the range 60 to 110° C. to effect decomposition of the cobalt ammine carbonate and precipitation of an insoluble cobalt compound selected from at least one of basic cobalt carbonate species and cobalt oxides onto said titania support, filtering a solid material from the aqueous solution, wherein the pH is maintained above 7.5 during the heating step, drying the solid material, and directly reducing the cobalt compound without a calcining step.

10. A catalyst comprising a cobalt species on a titania support and having upon reduction at 425° C., a cobalt metal surface area, as measured by hydrogen chemisorption at 150° C., in the range from 15 to 100 m$^2$ per gram total cobalt, made by mixing together said titania support and an aqueous solution of cobalt ammine carbonate at a pH in the range 7.5 to 12, and then heating said mixed together titania support and aqueous solution of cobalt ammine carbonate to a temperature in the range 60 to 110° C. to effect decomposition of the cobalt ammine carbonate and precipitation of an insoluble cobalt compound onto said titania support, wherein the pH is maintained above 7.5 during the heating step, further comprising directly reducing the cobalt compound without a calcining step.

11. A catalyst according to claim 10 having a cobalt metal surface area in the range from 20 to 40 m$^2$ per gram total cobalt.

12. A catalyst according to claim 10 wherein the titania is a coating on a silica or alumina support.

13. A catalyst according to claim 12 wherein the titania coating is present as a coating of 0.5 to 5 monolayers of titania on the underlying support.

14. A catalyst comprising elemental cobalt on a titania support and having, upon reduction at 425° C., a cobalt metal surface area, as measured by hydrogen chemisorption at 150° C., in the range from 15 to 100 $m^2$ per gram total cobalt, made by mixing together said titania support and an aqueous solution of cobalt ammine carbonate at a pH in the range 9 to 12, and then heating said mixed together titania support and aqueous solution of cobalt ammine carbonate to a temperature in the range 60 to 110° C. to effect decomposition of the cobalt ammine carbonate and precipitation of an insoluble cobalt compound selected from basic cobalt carbonate species and/or cobalt oxides onto said titania support, wherein the pH is maintained above 7.5 during the heating step, filtering a solid material from the aqueous solution, drying the solid material, and directly reducing the cobalt compound without a calcining step.

* * * * *

UNITED STATES PATENT AND TRADEMARK OFFICE
CERTIFICATE OF CORRECTION

PATENT NO. : 7,851,404 B2  Page 1 of 1
APPLICATION NO. : 10/528527
DATED : December 14, 2010
INVENTOR(S) : Cornelis Martinus Lok It is certified that error appears in the above-identified patent and that said Letters Patent is hereby corrected as shown below:

Title Page, item [56] "References Cited" under "Other Publications", fourth citation:

PCT/FB01/01811 should read --PCT/GB01/01811--

Signed and Sealed this
Thirteenth Day of September, 2011

David J. Kappos
*Director of the United States Patent and Trademark Office*